(12) United States Patent
Bonham et al.

(10) Patent No.: US 10,918,491 B2
(45) Date of Patent: Feb. 16, 2021

(54) REPLACEMENT KNEE COMPONENT

(71) Applicant: Invibio Knees Limited, Thornton Cleveleys Lancashire (GB)

(72) Inventors: Stephen Bonham, Thornton Cleveleys Lancashire (GB); Adam Briscoe, Thornton Cleveleys Lancashire (GB); Ian Revie, Thornton Cleveleys Lancashire (GB); Irene Sinz, Thornton Cleveleys Lancashire (GB); Reto Lerf, Langendorf (CH); Daniel Delfosse, Jegenstorf (CH)

(73) Assignee: INVIBIO KNEES LIMITED, Thornton Cleveleys Lancashire (GB)

( * ) Notice: Subject to any disclaimer, the term of this patent is extended or adjusted under 35 U.S.C. 154(b) by 210 days.

(21) Appl. No.: 16/081,360

(22) PCT Filed: Feb. 28, 2017

(86) PCT No.: PCT/GB2017/050530
§ 371 (c)(1),
(2) Date: Aug. 30, 2018

(87) PCT Pub. No.: WO2017/149286
PCT Pub. Date: Sep. 8, 2017

(65) Prior Publication Data
US 2020/0246151 A1    Aug. 6, 2020

(30) Foreign Application Priority Data
Mar. 2, 2016  (GB) .................................. 1603608

(51) Int. Cl.
*A61F 2/38*    (2006.01)
*A61F 2/30*    (2006.01)

(52) U.S. Cl.
CPC .. *A61F 2/3859* (2013.01); *A61F 2002/30014* (2013.01); *A61F 2002/30317* (2013.01);
(Continued)

(58) Field of Classification Search
CPC . A61F 2/3859; A61F 2/389; A61F 2002/3863
See application file for complete search history.

(56) References Cited

U.S. PATENT DOCUMENTS

| 4,215,439 A | 8/1980 | Gold et al. |
| 4,714,473 A | 12/1987 | Bloebaum |

(Continued)

FOREIGN PATENT DOCUMENTS

| DE | 19755776 A1 | 7/1999 |
| EP | 4215439 A1 | 10/2003 |

(Continued)

OTHER PUBLICATIONS

International Search Report and Written Opinion of corresponding International Application No. PCT/GB2017/050530; dated Jun. 13, 2017; 11 pages.

(Continued)

*Primary Examiner* — Bruce E Snow
*Assistant Examiner* — Melissa A Hoban
(74) *Attorney, Agent, or Firm* — Shumaker, Loop & Kendrick, LLP

(57) ABSTRACT

The invention relates to a femoral component (1) of a knee replacement assembly. The knee replacement assembly is arranged to articulate about an articulation axis (X). The femoral component comprises an outer surface (100), wherein the outer surface is arranged to define a replacement condyle; and an inner surface (200), opposed to the outer surface, wherein the inner surface is adapted for attachment to a prepared distal femur. The inner surface comprises portions (210, 220, 230, 240) provided with mutually- (Continued)

parallel ridges (201) and grooves (202). The ridges and grooves are arranged to provide an increased or reduced stiffness of the femoral component when cantilevered about the articulation axis compared with a stiffness of the femoral component when cantilevered about a transverse axis.

14 Claims, 11 Drawing Sheets

(52) U.S. Cl.
CPC ........... *A61F 2002/30827* (2013.01); *A61F 2002/30828* (2013.01); *A61F 2002/30879* (2013.01)

(56) References Cited

U.S. PATENT DOCUMENTS

| | | | | |
|---|---|---|---|---|
| 4,769,040 A * | 9/1988 | Wevers | ............... | A61F 2/389 623/20.32 |
| 5,755,799 A | 5/1998 | Oehy et al. | | |
| 6,893,467 B1 * | 5/2005 | Bercovy | ............... | A61F 2/3868 623/20.14 |
| 6,911,044 B2 * | 6/2005 | Fell | ............... | A61F 2/38 623/14.12 |
| 7,105,026 B2 * | 9/2006 | Johnson | ............... | A61F 2/38 623/20.14 |
| 7,947,082 B2 * | 5/2011 | Guidera | ............... | A61F 2/3868 623/20.33 |
| 9,162,008 B2 * | 10/2015 | Serafin, Jr. | ............... | B28B 11/24 |
| 10,653,527 B1 * | 5/2020 | Serafin, Jr. | ............... | A61F 2/3609 |
| 2007/0179627 A1 * | 8/2007 | Gustilo | ............... | A61F 2/30734 623/20.15 |
| 2008/0004709 A1 * | 1/2008 | O'Neill | ............... | B33Y 10/00 623/20.35 |
| 2008/0058948 A1 * | 3/2008 | Biegun | ............... | A61F 2/3859 623/20.35 |
| 2012/0323334 A1 * | 12/2012 | Jones | ............... | A61F 2/3859 623/20.35 |
| 2014/0121780 A1 | 5/2014 | Faure et al. | | |
| 2014/0277549 A1 | 9/2014 | Ell | | |
| 2015/0041566 A1 | 2/2015 | Shen et al. | | |
| 2016/0235543 A1 * | 8/2016 | Hwa | ............... | A61F 2/389 |
| 2017/0105848 A1 * | 4/2017 | Wogoman | ............... | A61B 17/1604 |
| 2017/0165076 A1 * | 6/2017 | Magagnoli | ............... | A61F 2/3859 |

FOREIGN PATENT DOCUMENTS

| | | |
|---|---|---|
| EP | 1836997 A1 | 9/2007 |
| GB | 1515022 A | 6/1978 |

OTHER PUBLICATIONS

UK Search Report of corresponding priority application No. GB1603608.9; dated Aug. 10, 2016; 4 pages.

* cited by examiner

Section A-A

Section B-B

REPLACEMENT KNEE COMPONENT

CROSS-REFERENCE TO RELATED APPLICATIONS AND PRIORITY

The present application claims priority from Great Britain Patent Application No. 1603608.9 filed on Mar. 2, 2016 and International Application No. PCT/GB2017/050530 filed on Feb. 28, 2017, both of which are hereby expressly incorporated by reference in their entireties.

FIELD

The present invention relates to a replacement component of a knee replacement assembly. In particular it relates to a replacement component having an anisotropic stiffness.

BACKGROUND TO THE INVENTION

Typically, knee replacement (also known as knee arthroplasty) is a major surgical procedure to replace load-bearing surfaces of a knee joint, usually to relieve pain and/or disability resulting from disease (e.g. osteoarthritis, rheumatoid arthritis, psoriatic arthritis) and/or trauma.

In general, the surgical procedure includes replacement of diseased and/or damaged joint surfaces (e.g. distal femur and/or proximal tibia with distal and proximal referring to the ends of the bones relative to the hips, so the distal femur is the end of the femur furthest from the hip and the proximal tibia the end of the tibia closest to the hip, jointed to the femur) with replacement components, such as femoral and tibial components, of a knee replacement assembly. The replacement components are typically shaped to allow articulation of the knee joint about an articulation axis of the knee replacement assembly. Knee replacement may be performed as a total knee replacement, in which surfaces of the distal femur and the proximal tibia are replaced, or as a partial knee replacement, in which surfaces of the distal femur or the proximal tibia are replaced.

Typically, anterior and/or posterior regions of the lateral and/or posterior condyles of the distal femur may be removed, thereby exposing a prepared surface. The removed regions may be replaced with a femoral component, which thereby replaces cortical bone and/or cartilage of the distal femur. The femoral component may be attached to the prepared surface mechanically (e.g. by fasteners), chemically (e.g. by cementing) and/or biologically (e.g. by bone in-growth). Similarly, the proximal tibia may be prepared and a tibial component may be attached to the prepared proximal tibia.

However, in use, a stress shielding effect of an attached component may cause bone loss (e.g. by resorption) of bone proximal the attached component. For example, stress shielding due to the attached femoral component may cause bone loss of the distal femur proximal the attached femoral component. This bone loss may result in eventual detachment of the attached femoral component from the distal femur, thereby compromising integrity of the knee joint. Thus, surgical replacement of the femoral component, together with possibly reconstruction of the distal femur, may be required to restore integrity of the knee joint.

Hence, there is a need for knee replacement assemblies having reduced failure rates in use.

SUMMARY OF THE INVENTION

It is one aim of the present invention, amongst others, to provide a component of a replacement knee assembly which at least partially obviates or mitigates at least some of the disadvantages of the prior art, whether identified herein or elsewhere. For instance, it is an aim of embodiments of the invention to provide a component that reduces stress shielding effects in use such that bone loss adjacent to the attached component is reduced, extending an effective life of the component. It is a further aim of embodiments of the invention to provide a component that remains better attached in use, thereby reducing a likelihood of further surgical intervention, whether a human or an animal patient. In particular it is an aim of the invention to provide a component which has an elastic modulus similar in value to that of bone, and where the stiffness of the component when flexed about the anterior-posterior (AP) axis is similar in value to the stiffness of the bone removed from the distal femur and replaced by the component.

A first aspect of the invention provides a femoral component of a knee replacement assembly, the knee replacement assembly arranged to articulate about an articulation axis, the femoral component comprising: an outer surface, wherein the outer surface is arranged to define a replacement condyle; and an inner surface, opposed to the outer surface, wherein the inner surface is adapted for attachment to a prepared distal femur; wherein the inner surface comprises portions provided with mutually-parallel ridges and grooves; and wherein the ridges and grooves are arranged to provide an increased or reduced stiffness of the femoral component when cantilevered about the articulation axis compared with a stiffness of the femoral component when cantilevered about a transverse axis.

A further aspect of the invention provides a method of treatment by surgery, wherein the method comprises: preparing a distal femur for attachment of a femoral component according to the first aspect of the invention; and attaching the femoral component to the prepared distal femur.

DETAILED DESCRIPTION OF THE INVENTION

According to the present invention there is provided a femoral component as set forth in the appended claims. Also disclosed is a method of treatment by surgery, comprising attaching the femoral component to a prepared distal femur. Other features of the invention will be apparent from the dependent claims, and the description that follows.

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention, such as colourants, and the like.

The term "consisting of" or "consists of" means including the components specified but excluding other components.

Whenever appropriate, depending upon the context, the use of the term "comprises" or "comprising" may also be taken to include the meaning "consists essentially of" or "consisting essentially of", and also may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

The first aspect of the invention provides a femoral component of a knee replacement assembly, the knee replacement assembly arranged to articulate about an articulation axis, the femoral component comprising:

an outer surface, wherein the outer surface is arranged to define a replacement condyle; and an inner surface, opposed to the outer surface, wherein the inner surface is adapted for attachment to a prepared distal femur;

wherein the inner surface comprises portions provided with mutually-parallel ridges and grooves; and wherein the ridges and grooves are arranged to provide an increased or reduced stiffness of the femoral component when cantilevered about the articulation axis compared with a stiffness of the femoral component when cantilevered about a transverse axis.

Most preferably, the ridges and grooves are arranged to provide an increased stiffness of the femoral component when cantilevered about the articulation axis compared with a stiffness of the femoral component when cantilevered about a transverse axis.

While aspects of the invention are described with reference to the femoral component, it must be understood that this is for convenience only and that the invention may similarly relate to a tibial component for a proximal tibia with the terms and features interpreted mutatis mutandis.

The femoral component may be a femoral component for humans or animals, particularly for humans.

It should be understood that the knee replacement assembly may comprise one or more components, such as the femoral component and/or a tibial component. Alternatively the knee replacement assembly may consist of the femoral component. Further, it should be understood that the articulation axis is that of a healthy knee, for example a human knee, allowing flexion and extension of a leg. Further it should be understood that the outer surface is an articulation surface. Thus, the outer surface may articulate against another component, for example a tibial component, or a healthy proximal tibia.

It should be understood that the outer surface may define a lateral condyle and/or a medial condyle, as would be present for a healthy distal femur. In addition, it should be understood that the inner surface is not limited in adaptation for attachment to the prepared distal femur. Rather, the distal femur may be prepared such that the distal femur is arranged to receive and/or be attached to the inner surface.

Herein, the term "ridge" is meant to refer to a feature standing proud of a basal surface of the portion, and may include a rib, for example, comprising an elongate protrusion from the portion of the inner surface. Herein, the term "groove" may include a furrow or channel, for example, an elongate cavity or void, formed in the portion or formed between adjacent ridges. It will be understood that only ridges or only grooves may be provided in or on the portion, with the respective complementary grooves or ridges arising as a result of the presence of the other component. So, for instance, two spaced mutually parallel ridges provided on a basal surface inherently form a complementary groove positioned between the two ridges.

The term "portion" as used herein may be considered for example as a region of the inner surface, and will typically be a central region of an inner surface of a lobe, as described below.

The increased stiffness of the femoral component when cantilevered about the articulation axis may be similarly presented when, for example, the femoral component is loaded in other bending configurations, such as three point and/or four point end tests. Furthermore, the femoral component may be loaded such that the outer surface or the inner surface is in compression, such that the inner surface and the outer surface are thus in tension, respectively. The transverse axis is transverse (i.e. not parallel to) to the articulation axis, and may be orthogonal to the articulation axis and to the long axis of the femur.

The term "cantilevered about the articulation axis" means that the bending used to measure stiffness is applied as if the component were being bent around the articulation axis. This is explained further below with reference to FIG. 10A.

The relatively increased stiffness of the femoral component when cantilevered about the articulation axis compared with when cantilevered about the transverse axis provides a mechanical behaviour of the femoral component that may better correspond to that of cortical bone and/or cartilage removed from the distal femur. That is, a directionality of the stiffness of the femoral component may better match that of a healthy distal femur, for example. In other words, the femoral component has an anisotropic stiffness that may better simulate local mechanical properties of the distal femur. In this way, a stress shielding effect due to the femoral component in use may be reduced, thereby reducing and/or retarding loss of bone of the distal femur adjacent to the femoral component. In this way, attachment of the femoral component to the distal femur may be for an extended period of use, since integrity of the knee may be better maintained. Thus, a failure rate of the femoral component may be reduced and hence replacement of the femoral component may be deferred. Thus, a patient may be less likely to need to undergo successive surgery so as to restore articulation of the knee.

As will be understood by the person skilled in the art, the femoral component may be provided in various sizes, such that an appropriate size may be selected for the prepared distal femur. For example, the femoral component may be available in sizes such as XS, S, A, B, C, D, E and/or F. Sizes of the portions provided with the ridges and the grooves may scale according to a size of the femoral component. Alternatively, the sizes of the portions provided with the ridges and grooves may not scale according to the size of the femoral component.

The femoral component may be a substantially U-shaped channel, having a longitudinal axis aligned with the articulation axis. The femoral component may comprise a longitudinal part extending from a lateral edge of the femoral component to a medial edge of the femoral component. The longitudinal part may comprise one or more dowels, pegs or male portions extending from the inner surface, arrangeable for insertion into corresponding, apertures, bores or female portions provided in the distal femur, for instance by drilling into the distal femur. The femoral component may further comprise one or more lobes, as described in more detail below, wherein the portions are portions of the inner surfaces of the lobes.

The femoral component may comprise one or more anterior lobes and/or one or more posterior lobes. For example, the femoral component may comprise an anterior medial lobe, a posterior medial lobe, and anterior lateral lobe and/or a posterior lateral lobe. The lobes may extend circumferentially away from the longitudinal part around the articulation axis. In this way, the lobes may be curved. The posterior lobes, arranged on a posterior site of the femoral component, may be similarly-sized and/or may be substantially C-shaped. The posterior lobes may be spaced apart, thereby separated across an intercondylar fossa of the distal femur in use. The anterior lobes may be conjoined. The anterior lateral lobe may be relatively longer than the anterior medial lobe. In this way, the femoral component may better correspond to the distal femur.

As detailed above, the outer surface of the femoral component is arranged to define a replacement condyle, generally two condyles per knee being provided, thus provides an articular surface. In contrast, the inner surface of the femoral component provides an attachment surface, for attachment to the prepared distal femur, as described above. That is, functions of the outer surface and of the in the surface differ. Particularly, material and/or mechanical and/or structural properties of and/or for these surfaces may be optimised for these functions, as described below.

As detailed above, the outer surface is arranged to define a replacement condyle (e.g. a lateral condyle, a medial condyle, a unicondyle). Hence, the outer surface femoral component may be substantially convex and may comprise outer surfaces of the lobes and/or longitudinal part, as described above, for example, outer surfaces of the anterior medial lobe, the posterior medial lobe and/or a medial part an inferior surface of the longitudinal part may define a replacement medial condyle. Similarly, outer surfaces of the anterior lateral lobe, the posterior lateral lobe and/or a lateral part of the inferior surface of the longitudinal part may define a replacement lateral condyle. That is, the femoral component may define a lateral condyle and a medial condyle, consistent with the distal femur, for articulation with a proximal tibia or a replacement tibial component or an inlay. Alternatively, the outer surface may define a unicondylar surface, providing an alternative geometry to the distal femur, for articulation with a corresponding replacement tibial component for a corresponding inlay.

As detailed above, the inner surface of the femoral component is adapted for attachment to a prepared distal femur i.e. the inner surface provides the attachment surface. The inner surface of the femoral component may be substantially concave. Thus, the portions provided with the ridges and the grooves may be substantially concave, located on the inner surfaces of the lobes. In this way, the ridges and the grooves may be provided on a substantially concave inner surface, such that the ridges and the grooves may follow the curvature of the inner surfaces of the lobes.

The portions provided with mutually parallel ridges and grooves may, for instance, occupy at least 50% of the inner surface area of each lobe, such as at least 70%, for instance at least 80% and up to 100%. The longitudinal part, provided with dowels or pegs, may be free from the portions provided with ridges and grooves. Overall, the proportion of the inner surface area of the femoral component occupied by the portions may be from 20 to 80%, with the portions on the inner surfaces of the lobes.

The ridges provide an increased stiffness (i.e. a reduced compliance) of the femoral component when cantilevered about the articulation axis, as compared to a component without ridges. Conversely, the grooves provide a reduction in stiffness (i.e. an increase compliance) of the femoral component when cantilevered that about the transverse axis, as compared to a component without grooves. Hence, the ridges and the grooves are arranged to provide the increased stiffness of the femoral component when cantilevered about the articulation axis compared with thickness of the femoral component when cantilevered about the transverse axis. In other words, the ridges and the grooves provide anisotropy (e.g. structural or mechanical anisotropy) to the portions on the inner surface of the femoral component, by providing directionality to the structural and mechanical properties of the femoral component.

The ridges may provide directional reinforcement to the portions in the inner surface of the femoral component. For example, the ridges may provide directional reinforcement to the portions on the inner surfaces of the femoral component, for instance to the lobes. For example, by providing reinforcement in the AP direction, the ridges may provide an increased stiffness when loaded along the AP direction.

Conversely, the grooves may not provide reinforcement. Rather, the grooves may provide a reduced stiffness (i.e. an increased compliance) in the transverse direction. This way, the compliance transverse to an orientation of the length of the grooves may be relatively increased for given loading conditions. It will be understood that the ridges and grooves will act together to provide anisotropy.

The femoral component may be configured such that an AP stiffness of the lateral condyle may be greater than an AP stiffness of the medial condyle. An AP stiffness of an inferior part of the lateral condyle may be greater than an AP stiffness of a superior part of the lateral condyle. An AP stiffness of an inferior part of the medial condyle may be greater than an AP stiffness of a superior part of the medial condyle.

Thus, the mechanical behaviour of the femoral component may better correspond to that of cortical bone and/or cartilage removed from the distal femur and replaced by the femoral component this way, a stress shielding effect due to the femoral component in use may be reduced. In this way, a loss of bone adjacent to the femoral component may be reduced in use and thus attachment of the femoral component to the distal femur may be better maintained. Thus, a failure rate of the knee replacement assembly in use may be reduced.

A stiffness of the femoral component in the AP direction (i.e. the AP stiffness) may be from 50 N/mm to 1000 N/mm (i.e. from 50 kN/m to 1000 kN/m). Suitably, the AP stiffness may be from 100 N/mm to 400 N/mm (i.e. from 100 kN/m to 400 kN/m). More suitably, the AP stiffness may be about 259±109 N/mm (i.e. 259±109 kN/m), that is, from 150 N/mm to 368 N/mm (i.e. from 150 kN/m to 368 kN/m).

Three to twenty ridges may be provided. For example, the or each, lobe may comprise three to twenty ridges in its respective portion. Five to fifteen ridges, preferably seven to nine ridges may be provided. The portion may comprise a corresponding number of grooves. For example, the portion may comprise N ridges and N+1 grooves. By varying a number of the ridges and/or the grooves, the stiffness of the femoral component in the AP direction relative to the transverse direction may be adjusted and/or controlled.

The ridges may be equi-distantly spaced. That is, a spacing of the ridges may be constant. For example, the ridges may have a periodicity defined between centrelines of adjacent ridges. The grooves may have a groove width d, as defined between walls of adjacent ridges that is, the ridges may be spaced apart by a ridge spacing d.

Conversely, the ridges may be variably spaced. That is, a spacing of the ridges may be non-constant. For example, the ridge spacing may vary across a portion of a lobe. For example, the ridge spacing may be relatively larger near a lateral edge of the femoral component while the ridge spacing may be relatively smaller near a medial edge of the femoral component.

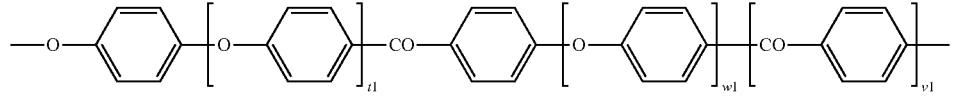

By varying a spacing of the ridges and/or the grooves, the stiffness of the femoral component in the AP direction relative to the transverse direction may be adjusted and/or controlled.

A section of the ridges may have dimensions in cross-section of a width w and a height h. The width w may be from 0.1 to 1 mm. Suitably, the width w may be from 0.2 to 0.9 mm. The height h may be from 1 to 3 mm. Suitably, the width w may be from 1.5 to 2.6 mm. An aspect ratio R of the ridge, defined as R=h/w, may thus be from 1 to 30. Suitably, the aspect ratio R of the ridge is from 1 to 10.

By modifying a profile (e.g. dimensions, symmetry) of the ridges and/or the grooves, the stiffness of the femoral component in the AP direction relative to the transverse direction may be adjusted and/or controlled.

The ridges and the grooves may be oriented in an anterior-posterior (AP) direction, transverse to the articulation axis. Alternatively, the ridges and the grooves may be oriented obliquely to the AP direction. In this way, a stiffness of the femoral component in the AP direction may be relatively higher than a stiffness of the femoral component in a transverse direction (e.g. the articulation axis). Conversely, a compliance of the femoral component in the AP direction may be relatively lower than a compliance of the femoral component in the transverse direction.

In this way, by altering an orientation of the ridges and/or the grooves, the stiffness of the femoral component in the AP direction relative to the transverse direction may be adjusted and/or controlled.

The portions may comprise other ridges and/or grooves, oriented transversely to the ridges and the grooves. In this way, by altering a distribution of the ridges and/or the grooves, the stiffness of the femoral component in the AP direction relative to the transverse direction may be adjusted and/or controlled.

The ridges may be continuous ridges and/or the grooves may be continuous grooves over the extent of each portion. Alternatively, the ridges may be discontinuous ridges and/or the grooves may be discontinuous grooves so that there are discontinuities within a portion.

The portions may extend between lobes. For example, the ridges and/or the grooves in the anterior lateral lobe may extend to the posterior lateral lobe.

In this way, by altering a continuity of the ridges and/or the grooves, the stiffness of the femoral component in the AP direction relative to the transverse direction may be adjusted and/or controlled.

The femoral component may be formed from a polymeric composition, the polymeric composition having an elastic modulus (i.e. a Young's modulus) from 3000 MPa to 5000 MPa. Suitably, the polymeric composition may have an elastic modulus of from 3500 to 4500 MPa.

The polymeric composition may comprise one or more polymers selected from a group consisting of: polyarylketone, polyacetal (POM), polyester, polyamide, polyurethane, polycarbonate, polyimide and polysulfone. Preferred polymers are polyarylketones.

Such preferred polymers comprises a repeat unit of formula (I):

wherein t1 and w1 independently represent 0 or 1 and v1 represents 0, 1 or 2.

The composition, may consist or consist essentially of the polymeric material, or may include, for instance from 60 to 100%, say from 75 to 100% of the polymeric material, with from 0 to 40%, say from 0 to 25% of other materials. The composition may include, for example colourants (e.g. pigments, ceramics, metal oxides (eg. titanium dioxide)) or fillers (for example reinforcing or wear enhancing fillers or fibres, bioactive fillers such as bioglasses, soluble glasses. When a filler is included in the composition, it may suitably be included to improve the mechanical properties and/or bonding characteristics and/or biological acceptability of the composition. However, it has been found that components with excellent mechanical properties can be made without requiring addition of filler. Preferably, the composition comprises at least 80 wt %, at least 90 wt % or at least 94 wt % of the polymeric material.

The polymeric material preferably consists essentially of a repeat unit of formula I. Preferred polymeric materials comprise (or consist essentially of) a repeat unit wherein t1=1, v1=0 and w1=0; t1=0, v1=0 and w1=0; t1=0, w1=1, v1=2; or t1=0, v1=1 and w1=0. More preferred polymeric materials comprise (or consist essentially of) a repeat unit wherein t1=1, v1=0 and w1=0; or t1=0, v1=0 and w1=0. A particularly preferred polymeric material comprises (or consists essentially of) a repeat unit wherein t1=1, v1=0 and w1=0.

In preferred embodiments, the polymeric material is selected from polyetheretherketone, polyetherketone, polyetherketoneetherketoneketone and polyetherketoneketone. In a more preferred embodiment, the polymeric material is selected from polyetherketone and polyetheretherketone. In another preferred embodiment, the polymeric material is polyetheretherketone.

The polymeric material may have a Notched Izod Impact Strength (specimen 80 mm×10 mm×4 mm with a cut 0.25 mm notch (Type A), tested at 23° C., in accordance with ISO180) of at least 4 KJm$^{-2}$, preferably at least 5 KJm$^{-2}$, more preferably at least 6 KJm$^{-2}$. The Notched Izod Impact Strength may be less than 10 KJm$^{-2}$, suitably less than 8 KJm$^{-2}$. The Notched Izod Impact Strength may be at least 3 KJm$^{-2}$, suitably at least 4 KJm$^{-2}$, preferably at least 5 KJm$^{-2}$. The impact strength may be less than 50 KJm$^{-2}$, suitably less than 30 KJm$^{-2}$.

The polymeric material suitably has a melt viscosity (MV) of at least 0.06 kNsm$^{-2}$, preferably has a MV of at least 0.09 kNsm$^{-2}$, more preferably at least 0.12 kNsm$^{-2}$, or at least 0.15 kNsm$^{-2}$. Advantageously, the MV may be at least 0.35 kNsm$^{-2}$ and/or at least 0.40 kNsm$^{-2}$. An MV of about 0.45 kNsm$^{-2}$ has been found to be particularly advantageous in the manufacture of accurate, strong components.

MV is suitably measured using capillary rheometry operating at 400° C. at a shear rate of 1000 s$^{-1}$ using a tungsten carbide die, 0.5 mm×3.175 mm.

The polymeric material may have a MV of less than 1.00 kNsm$^{-2}$, preferably less than 0.5 kNsm$^{-2}$.

The polymeric material may have a MV in the range 0.09 to 0.5 kNsm$^{-2}$, preferably in the range 0.14 to 0.5 kNsm$^{-2}$, more preferably in the range 0.4 to 0.5 kNsm$^{-2}$.

The polymeric material may have a tensile strength, measured in accordance with IS0527 (specimen type 1b) tested at 23° C. at a rate of 50 mm/minute of at least 20 MPa, preferably at least 60 MPa, more preferably at least 80 MPa. The tensile strength is preferably in the range 80-110 MPa, more preferably in the range 80-100 MPa.

The polymeric material may have a flexural strength, measured in accordance with IS0178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-180 MPa, more preferably in the range 145-164 MPa.

The polymeric material may have a flexural modulus (i.e. Young's modulus measured by flexing), measured in accordance with IS0178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably from 3.0 to 5.0 GPa, more preferably from 3.5-4.5 GPa.

The polymeric material may be amorphous or semi-crystalline. It is preferably crystallisable. It is preferably semi-crystalline. The level and extent of crystallinity in a polymer is preferably measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning calorimetry (DSC).

The level of crystallinity of the polymeric material may be at least 1%, suitably at least 3%, preferably at least 5% and more preferably at least 10%. In preferred embodiments, the crystallinity may be greater than 25%. It may be less than 50% or less than 40%.

The main peak of the melting endotherm (Tm) of the polymeric material (if crystalline) may be at least 300° C.

For the polymeric material, it is preferred that t1=1, v1=0 and w1=0.

The polymeric composition may be a reinforced polymeric composition. The polymeric composition may comprise one or more polymers, as described above, and/or one or more fillers selected from a group comprising: fibres, particles and platelets. The polymeric composition may comprise from 60 to 100% by weight polymer and 0 to 40% by weight filler, such as 70 to 100% by weight polymer and 0 to 30% by weight filler. In some embodiments, the polymeric composition may consist or consist essentially of a polymer or of a blend of polymers. In some embodiments, the component may comprise different polymer compositions in different parts of the component, so for instance the inner surface may be formed from a different polymer composition than the outer surface. Preferred polymers for use in such combinations are selected from the polymers set out above.

A further aspect of the invention provides a method of treatment by surgery, wherein the method comprises:

preparing a distal femur for attachment of a femoral component according to the first aspect of the invention; and attaching the femoral component to the prepared distal femur.

BRIEF DESCRIPTION OF THE DRAWINGS

For a better understanding of the invention, and to show how exemplary embodiments of the same may be brought into effect, reference will be made, by way of example only, to the accompanying diagrammatic Figures, in which.

DETAILED DESCRIPTION OF THE DRAWINGS

Figure 1A:
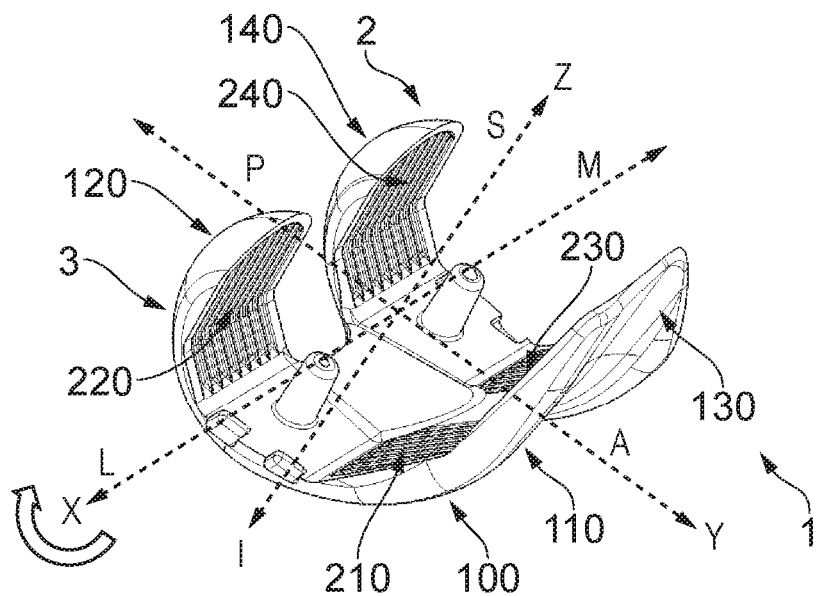
FIG. 1A schematically depicts a perspective view of a femoral component according to an exemplary embodiment of the invention.
Figure 1B:
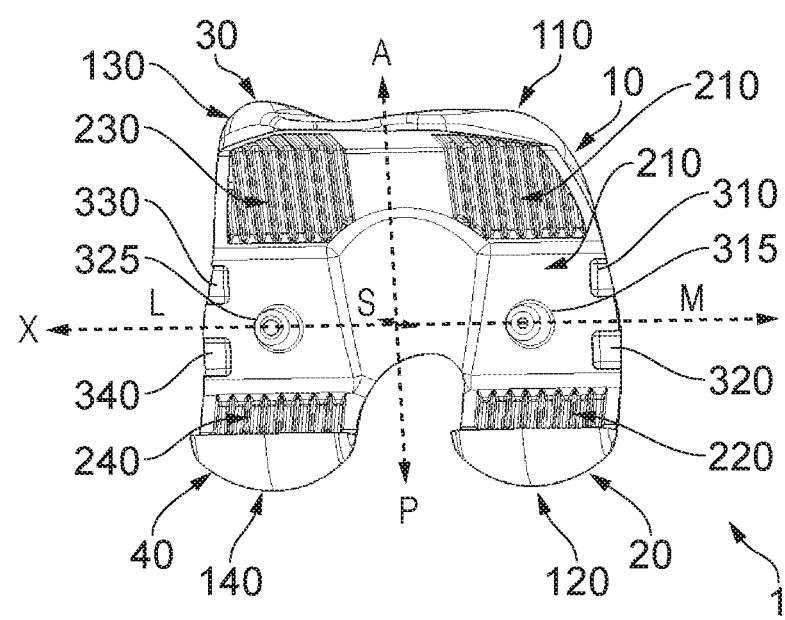
FIG. 1B schematically depicts an underneath perspective view of the femoral component of FIG. 1A.
Figure 1C:
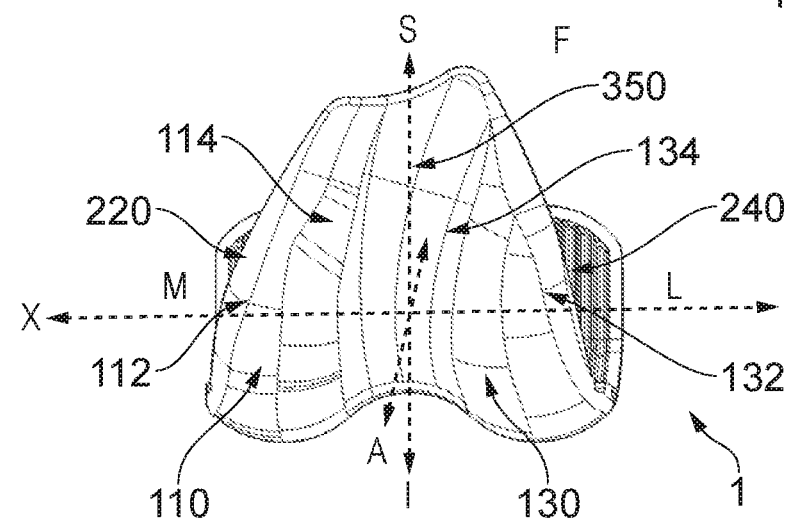
FIG. 1C schematically depicts an anterior perspective view of the femoral component of FIG. 1A.

FIGS. 1A-1C, show a femoral component 1 of a knee replacement assembly (not shown), the knee replacement assembly arranged to articulate about an articulation axis X. The femoral component 1 comprises an outer surface 100 and an inner surface 200, opposed to the outer surface 100. The outer surface 100 is arranged to define a replacement condyle (pair). The inner surface 200 is adapted for attachment to a prepared distal femur. Further, the inner surface 200 comprises portions 210, 220, 230, 240 provided with mutually-parallel ridges 201 and grooves 202. The ridges 201 and grooves 202 are arranged to provide an increased stiffness of the femoral component 1 when cantilevered about the articulation axis X compared with a stiffness of the femoral component 1 when cantilevered about a transverse axis. Thus, a mechanical behaviour of the femoral component 1 may better correspond to that of cortical bone and/or cartilage removed from the distal femur and replaced by the femoral component 1. In this way, a stress shielding effect due to the femoral component 1 in use may be reduced. Hence, a failure rate of the knee replacement assembly in use may be reduced.

For convenience, a set of three mutually-orthogonal axes may be defined for the femoral component 1. As detailed above, the knee replacement assembly is arranged to articulate about the articulation axis X, which is oriented in a lateral L-medial M (LM) direction. A first transverse axis Y, orthogonal to the articulation axis X, is oriented in an anterior A-posterior P (AP) direction. A second transverse axis Z, orthogonal to the articulation axis X and the first transverse axis Y, is oriented in a superior S-inferior I (SI)

direction e.g. oriented along a longitudinal axis of a femur, in use. Thus, the femoral component may be considered to have a lateral edge L, a medial edge M, an anterior side A, a posterior side P and an inferior side I.

In detail, the femoral component 1 is formed as a unitary structure from a polymeric composition. The femoral component 1 is a substantially U-shaped channel, having a longitudinal axis aligned with the articulation axis X. The femoral component 1 comprises a longitudinal part 300, extending from the lateral edge L of the femoral component 1 to the medial edge M of the femoral component 1. The longitudinal part 300 comprises two tapered dowels 315, 325, extending from a centreline of the inner surface 200, arranged for insertion into corresponding bores provided in the prepared distal femur. The longitudinal part 300 further comprises pairs of rectangular pockets 310 & 320, 330 & 340 provided on opposed sides of the centreline of the inner surface 200 at the medial edge M and the lateral edge L of the femoral component 1, respectively.

The femoral component 1 comprises an anterior medial lobe 10 and a posterior medial lobe 20, next to the medial edge M of the femoral component 1. The femoral component 1 further comprises an anterior lateral lobe 30 and a posterior lateral lobe 40, next to the lateral edge L of the femoral component 1. The anterior lobes 10, 30 are arranged on the anterior side A of the femoral component 1 and extend circumferentially away from the longitudinal part 300, around the articulation axis X. That is, the anterior lobes 10, 30 are curved. The posterior lobes 20, 40 are similarly-sized, substantially C-shaped and arranged on the posterior side P of the femoral component 1, extending circumferentially away from the longitudinal part 300, around the articulation axis X. That is, the posterior lobes 10, 30 are curved. While the posterior lobes 20, 40 are spaced apart, thereby separated across an intercondylar fossa of the distal femur in use, the anterior lobes 10, 30 are conjoined by a part 350. Furthermore, the anterior lateral lobe 30 is relatively longer than the anterior medial lobe 10.

While the outer surface 100 of the femoral component 1 provides an articular surface, as described below, the inner surface 200 of the femoral component 1 provides an attachment surface, for attachment to the prepared distal femur. That is, functions of the outer surface 100 and the inner surface 200 differ. Particularly, material and/or mechanical and/or structural properties for these surfaces may be optimised, as described below.

As detailed above, the outer surface 100 of the femoral component 1 provides the articular surface. Particularly, the substantially convex outer surface 100 of the femoral component 1 comprises outer surfaces 110, 120, 130, 140 of the lobes 10, 20, 30, 40 respectively and an outer surface of the longitudinal part 300 (i.e. an inferior surface). The outer surfaces of the anterior medial lobe 110, the posterior medial lobe 120 and a medial part of the inferior surface define a replacement medial condyle 2. Similarly, the outer surfaces of the anterior lateral lobe 130, the posterior lateral lobe 140 and a lateral part of the inferior surface define a replacement lateral condyle 3. Inferior and superior regions of the replacement medial condyle 2 and the replacement lateral condyle 3 may be defined. Thus, the outer surface of the anterior lateral lobe 130 comprises an inferior anterior lateral region 132 and a superior anterior lateral region 134. Similarly, the outer surface of the anterior medial lobe 110 comprises an inferior anterior medial region 112 and a superior anterior medial region 114. Similar regions for the posterior medial lobe 120 and the posterior lateral lobe 140 may be similarly defined. The replacement medial condyle 2 and the replacement lateral condyle 3 are arrangeable to articulate with respective condyles of a proximal tibia and/or a tibial component of the knee replacement assembly. Thus, the replacement medial condyle 2 and the replacement lateral condyle 3 have smooth surfaces (i.e. low roughness), free from protrusions, so as to minimize wear, as known to the person skilled in the art. In this way, the femoral component 1 renews the distal femur, by replacing diseased and/or damaged cortical bone and/or cartilage removed from the distal femur.

As detailed above, the inner surface 200 of the femoral component 1 provides the attachment surface. Particularly, the substantially concave inner surface 200 of the femoral component 1 comprises portions 210, 220, 230, 240 of the lobes 10, 20, 30, 40 respectively. These portions 210, 220, 230, 240 are provided with the ridges 201 and the grooves 202. The ridges 201 and the grooves 202 are oriented in the AP direction, parallel to the Y axis. Since the lobes 10, 20, 30, 40 extend circumferentially around the articulation axis X, the ridges 201 and the grooves 202 thus extend circumferentially around the articulation axis X in the portions 210, 220, 230, 240. That is, the ridges 201 are circumferential ridges 201 and the grooves 202 are circumferential grooves 202.

The ridges 201 provide the increased stiffness (i.e. a reduced compliance) of the femoral component 1 when cantilevered about the articulation axis X. Conversely, the grooves 202 provide a reduced stiffness (i.e. an increased compliance) of the femoral component 1 when cantilevered about the transverse axis, such as the Y or Z axes. Hence, the ridges 201 and grooves 202 are arranged to provide the increased stiffness of the femoral component 1 when cantilevered about the articulation axis X compared with the stiffness of the femoral component 1 when cantilevered about a transverse axis. That is, the ridges 201 and grooves 202 provide anisotropy (e.g. structural, mechanical) to the portions 210, 220, 230, 240 of the lobes 10, 20, 30, 40 respectively on the inner surface 200 of the femoral component 1.

Particularly, the ridges 201 provide directional (i.e. the AP direction) structural (i.e. mechanical) reinforcement to the lobes 10, 20, 30, 40, in the portions 210, 220, 230, 240 respectively on the inner surface 200 of the femoral component 1. In this way, deformation along the lobes 10, 20, 30, 40 about the longitudinal part 300 (i.e. about the articulation axis X) may be relatively reduced for given loading conditions (i.e. a force or stress distribution). That is, stiffnesses of the lobes 10, 20, 30, 40 when cantilevered about the longitudinal part 300 may be relatively increased.

Conversely, the grooves 202 do not provide reinforcement to the lobes 10, 20, 30, 40. Rather, the grooves 202 provide a reduced stiffness (i.e. an increased compliance) to the lobes 10, 20, 30, 40 in the transverse direction (e.g. the LM direction) to the AP direction. In this way, deformation across the lobes 10, 20, 30, 40 may be relatively increased for given loading conditions (i.e. a force or stress distribution). That is, compliances of the lobes 10, 20, 30, 40 when cantilevered about the medial or lateral sides (i.e. about the Y or Z axis) may be relatively increased.

Thus, the mechanical behaviour of the femoral component 1 may better correspond to that of cortical bone and/or cartilage removed from the distal femur and replaced by the femoral component 1. In this way, a stress shielding effect due to the femoral component 1 in use may be reduced. Hence, a failure rate of the knee replacement assembly in use may be reduced.

FIGS. 2A-2D show elevations and cross-sections of the posterior medial lobe 20 in more detail, by way of example. The anterior medial lobe 10, the posterior medial lobe 20 and/or the anterior lateral lobe 30 are arranged similarly to the posterior medial lobe 20. That is, an arrangement of the posterior medial lobe 20 is typical of the other lobes 10, 30, 40.

A rim 203 extends away from the inner surface 200 around a periphery of the lobe 20, surrounding the portion 220. The rim 203 provides reinforcement to the periphery of the posterior medial lobe 20 and provides a container for cement in the portion 220.

The portion 220 includes seven parallel, mutually-equispaced, straight ridges or ribs 201, that extend along the portion 220 from the longitudinal part 300. The ridges 201 are spaced apart by six grooves 202. Two additional grooves 202 space the outermost ridges 201 from the rim 203.

Figure 2A:
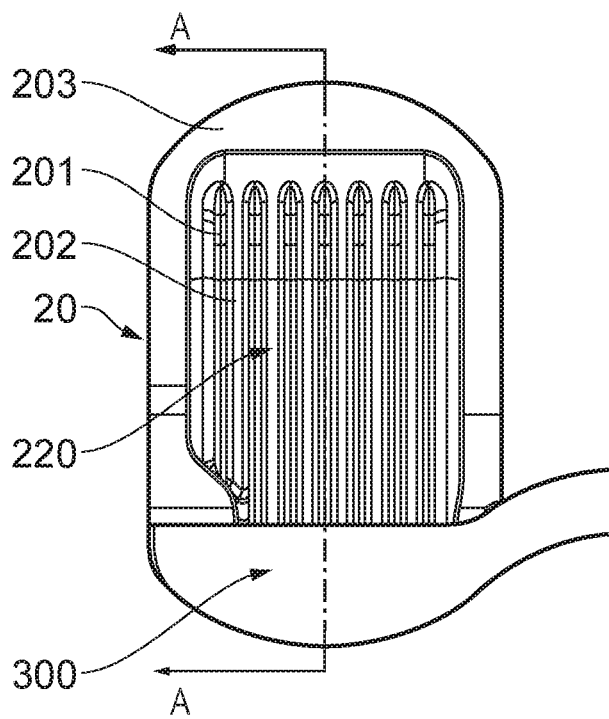
FIGS. 2A-2D schematically depict partial cross-sections of the femoral component of FIG. 1A.
Figure 2B:
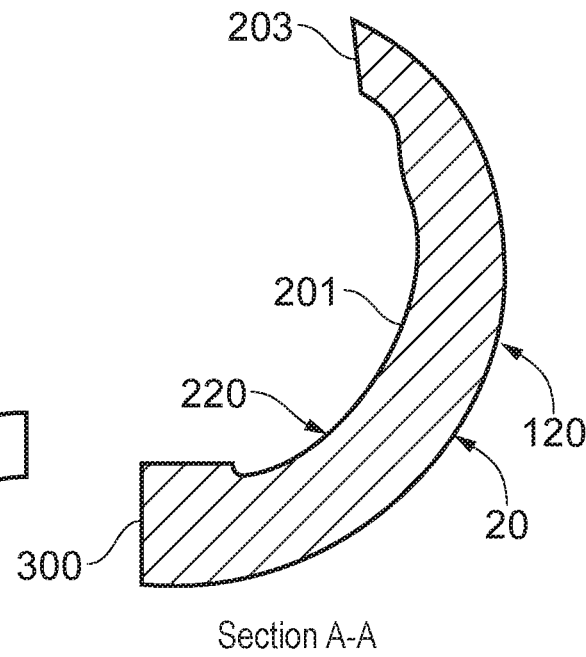

FIG. 2B shows a cross-section through the lobe 20, in the X axis i.e. on the YZ plane, as identified by Section A-A of FIG. 2A. The ridges 201 are defined by sweeping a section profile along a curvature of the lobe 20. A sweep curvature of the ridges 201 is derived by offsetting an external curvature of the posterior medial lobe 20, such that a height of the ridges 201 is substantially uniform in the portion 220. The ridges 201 are blended towards a free end of the lobe 20, such that the height of the ridges 201 reduces towards the free end of the lobe 20.

Figure 2C:
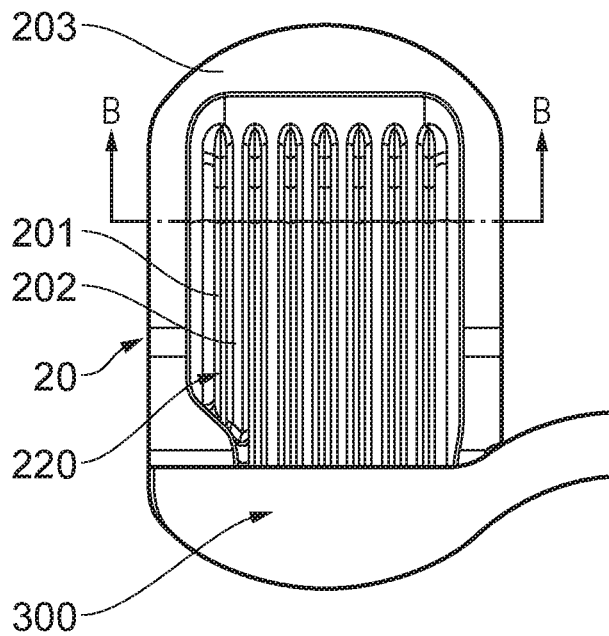
Figure 2D:
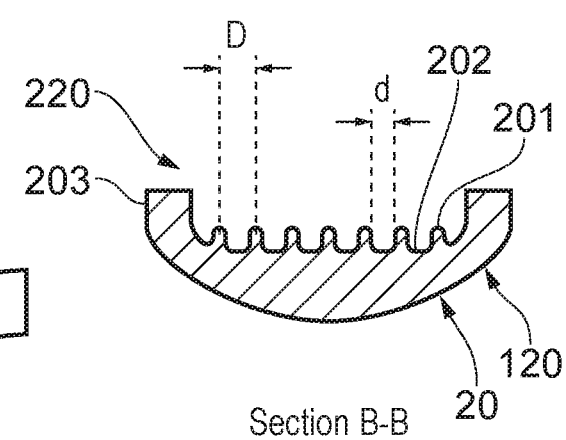

FIG. 2D shows a cross-section through the lobe 20, in the Z axis i.e. on the XY plane, as identified by Section B-B of FIG. 2C. The ridges 201 have a periodicity of D, as defined between centrelines of adjacent ridges 201. The grooves 202 have a groove width d, as defined between walls of adjacent ridges 201 i.e. the ridges are spaced apart by a ridge spacing d. The grooves 202 may be considered as furrows or channels in the portion 220.

Figure 3:
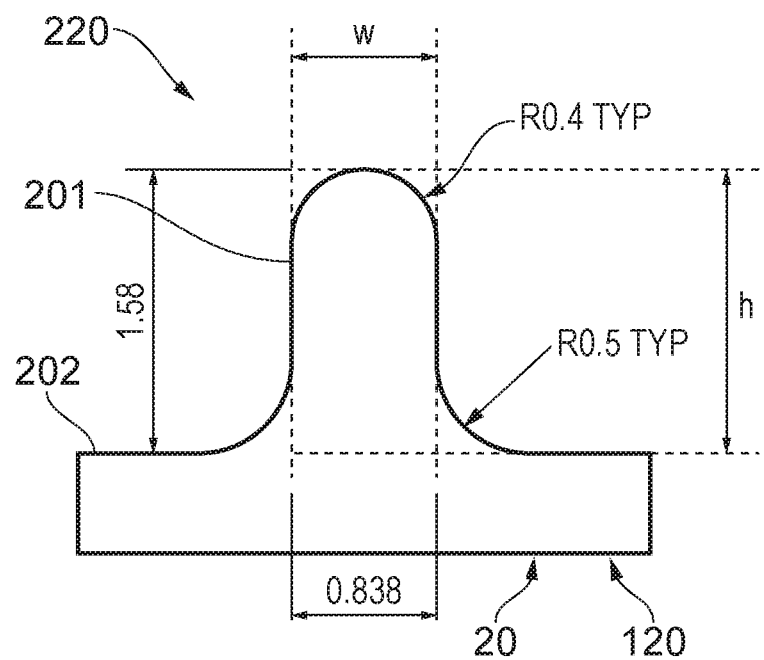
FIG. 3 schematically depicts a cross-section of a ridge of the femoral component of FIG. 1A.
Figure 4A:
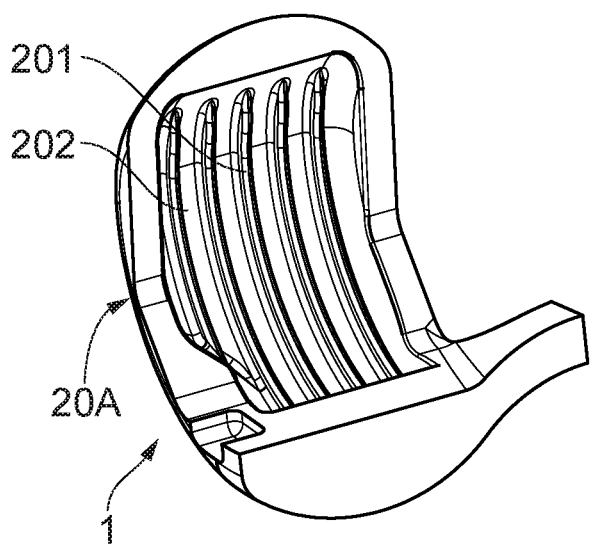
FIGS. 4A-4E schematically depict perspective views of a part of a femoral component according to other exemplary embodiments of the invention.
Figure 4B:
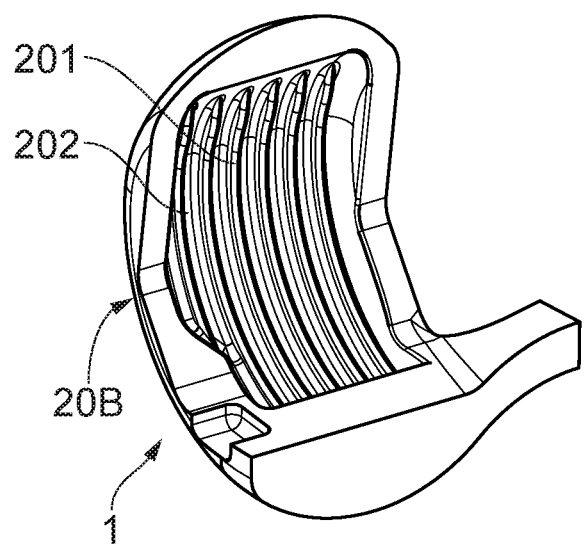
Figure 4C:
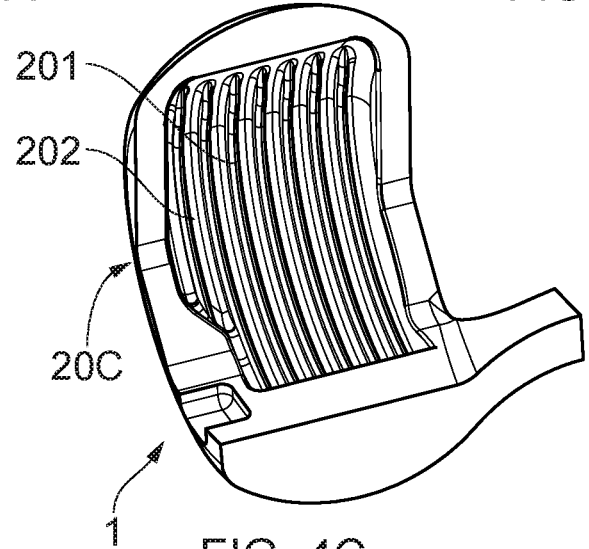
Figure 4D:
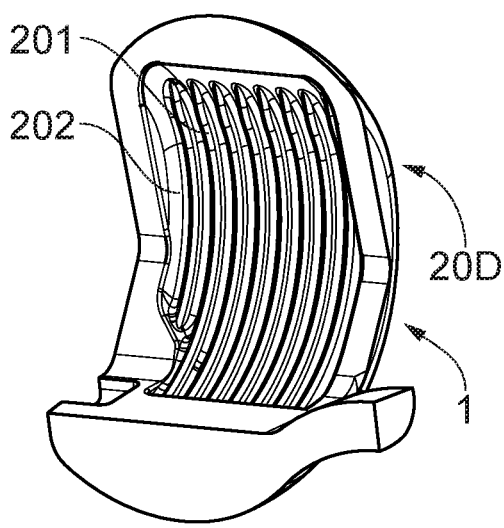
Figure 4E:
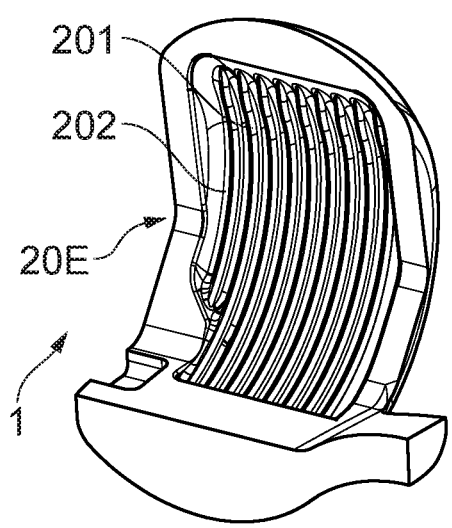
Figure 5A:
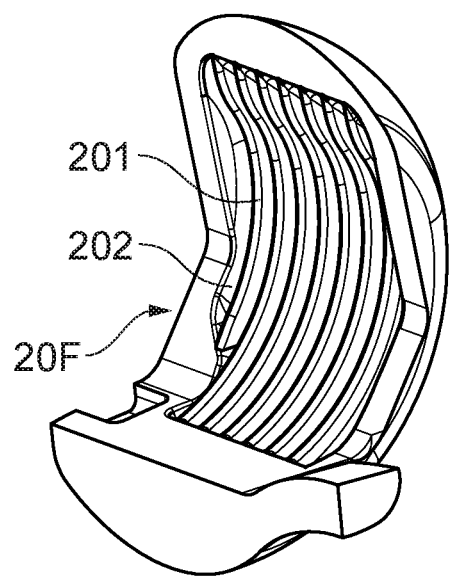
FIGS. 5A-5H schematically depict perspective views and cross-sections of a part of a femoral component according to other exemplary embodiments of the invention.
Figure 5B:
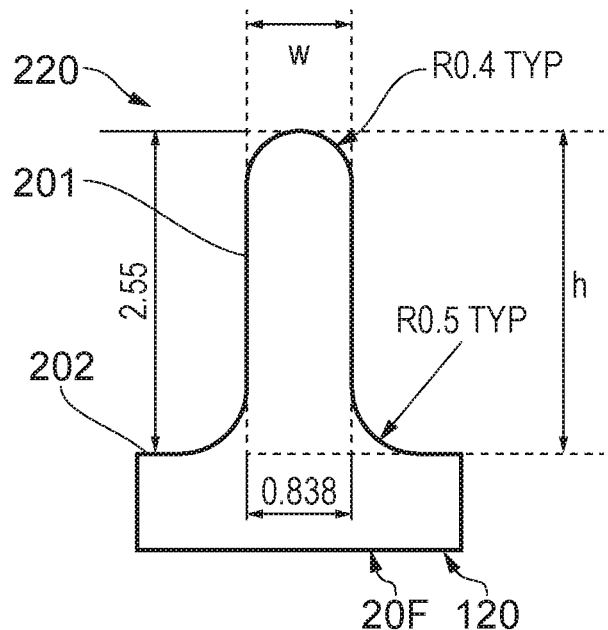
Figure 5C:
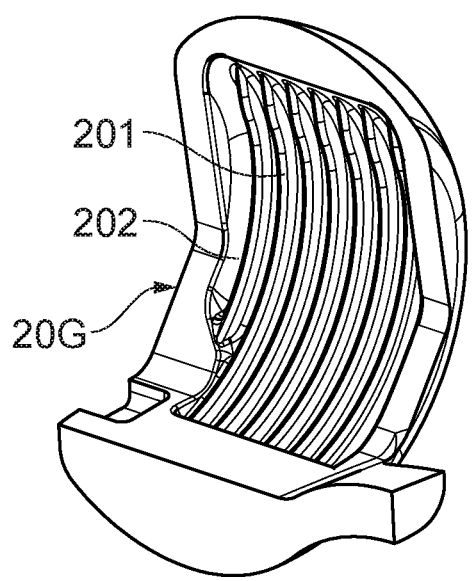
Figure 5D:
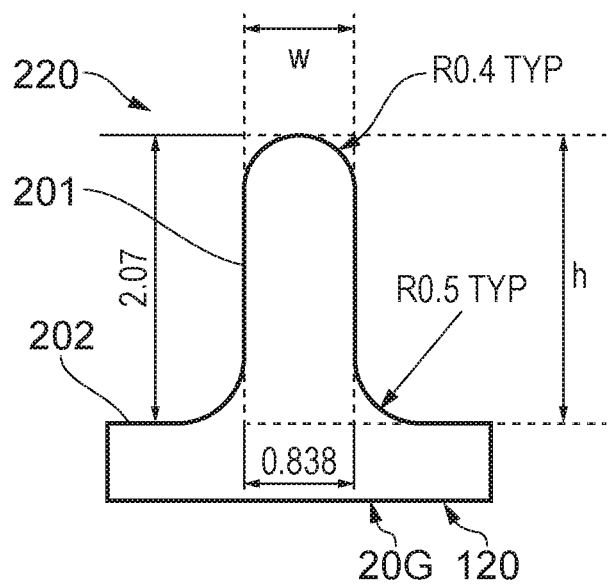
Figure 5E:
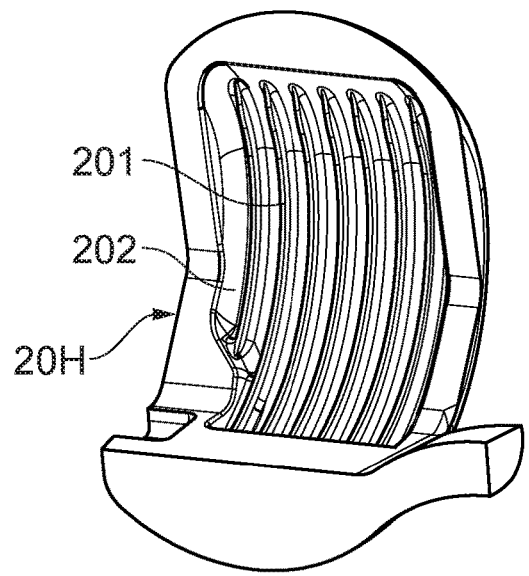
Figure 5F:
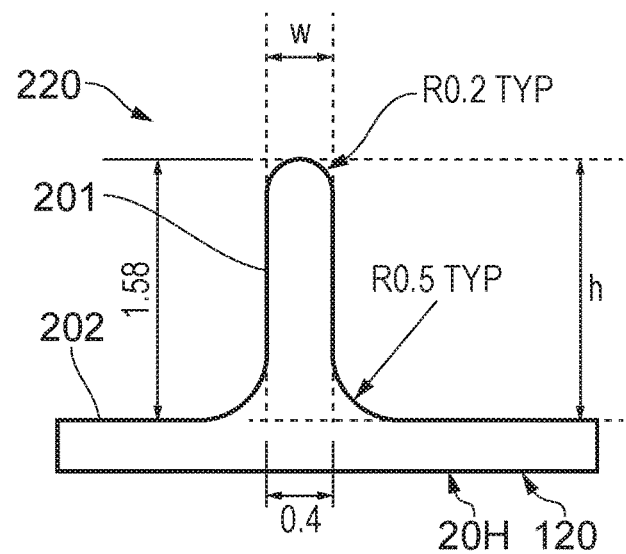
Figure 5G:
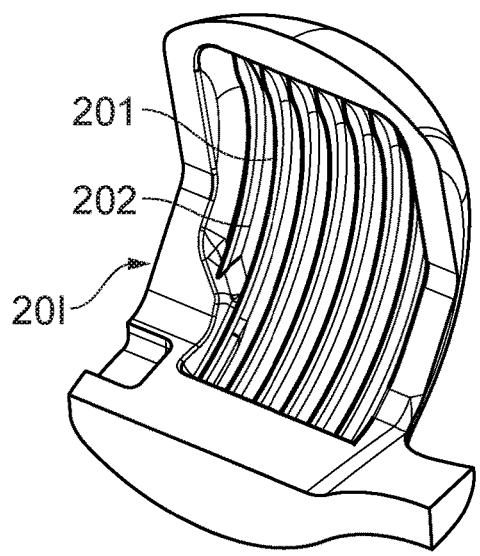
Figure 5H:
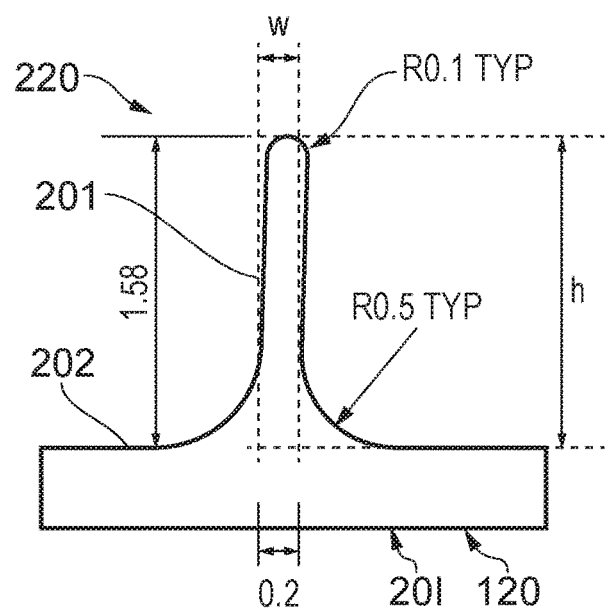
Figure 6A:
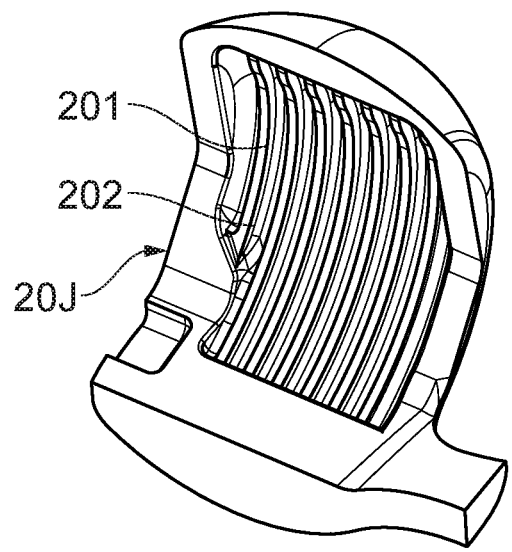
FIGS. 6A-6D schematically depict perspective views and cross-sections of a part of a femoral component according to other exemplary embodiments of the invention.
Figure 6B:
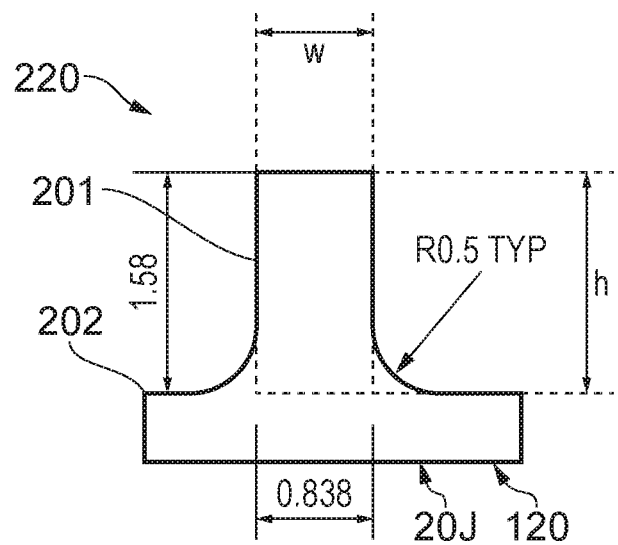
Figure 6C:
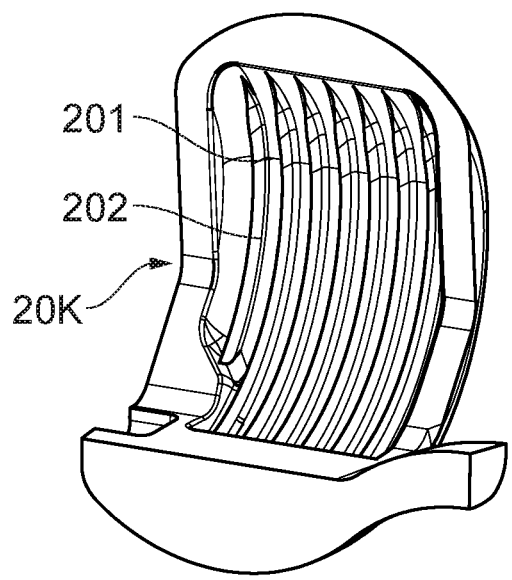
Figure 6D:
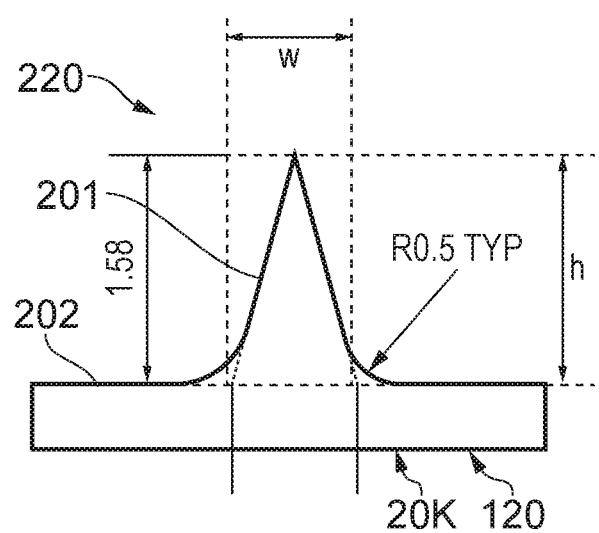

FIG. 3 shows a cross-section of one ridge 201 (i.e. a profile of the ridge 201) in more detail. The ridge 201 is symmetrical, having flat, substantially parallel sides and a rounded top. The sides of the ridge 201 have a minimum draft angle of 1. The ridge 201 has dimensions of a width w of 0.838 mm and a height h of 1.58 mm. Thus, the ridge 201 has an aspect ratio R=h/w=1.58/0.838~1.89. External edges (corners) of the ridge 201 are chamfered (e.g. radiused, radius 0.4 mm typical). Given the width w of 0.838 mm, the top of the ridge is thus substantially semicircular in cross-section. Internal edges (corners) of the ridge 201 are chamfered (e.g. radiused, radius 0.5 mm typical), to reduce stress-concentrations and/or facilitate manufacture.

FIGS. 4A-4E show alternative lobes 20A-20E in which a number of ridges 201 and grooves 202, as described above, is varied. In this way, the stiffness of the lobe 20 in the AP direction relative to the transverse direction may be adjusted and/or controlled.

Particularly, the lobes 20A-20E include five, six, seven, eight and nine ridges 201, respectively, and a corresponding number of grooves 202 (i.e. six, seven, eight, nine and ten grooves 202, respectively). A size and a shape of the ridges 201 of the lobes 20A-20E are as described above with reference to FIG. 3. Hence, the groove width d of the grooves 202 is correspondingly reduced as the number of ridges 201 is increased, since the width w of the ridges 201 is constant.

In this way, by varying the number of ridges 201 and/or grooves 202, the stiffness of the lobe 20 in the AP direction relative to the transverse direction may be adjusted and/or controlled.

FIGS. 5A-5H show alternative lobes 20F-20I in which dimensions of the ridges 201 and the grooves 202, as described above, is adjusted. In this way, the stiffness of the lobe 20 in the AP direction relative to the transverse direction may be adjusted and/or controlled.

Particularly, the lobes 20F-20I have seven ridges 201 and a corresponding number of grooves 202 (i.e. eight grooves 202). Table 1 summarises dimensions of the ridges 201. Since the number of ridges 201 is constant (e.g. seven), the groove width d of the grooves 202 is correspondingly adjusted as the width w of the ridges 201 is adjusted. For example, increasing the width w of the ridges 201 for a constant number of ridges 201 reduces the groove width d of the grooves 202. Conversely, decreasing the width w of the ridges 201 for a constant number of ridges 201 increases the groove width d of the grooves 202. In this way, by adjusting dimensions of the ridges 201 and/or the grooves 202, the stiffness of the lobe 20 in the AP direction may be adjusted and/or controlled.

TABLE 1

Dimensions of the ridges 201 of the lobes 20, 20F, 20G, 20H, 20I.

| Lobe | Ridge 201 height h/mm | Ridge 201 width w/mm | Aspect ratio R | External radius/ mm | Internal radius/ mm |
|---|---|---|---|---|---|
| 20 | 1.58 | 0.838 | 1.89 | 0.4 | 0.5 |
| 20F | 2.55 | 0.838 | 3.04 | 0.4 | 0.5 |
| 20G | 2.07 | 0.838 | 2.47 | 0.4 | 0.5 |
| 20H | 1.58 | 0.4 | 3.95 | 0.2 | 0.5 |
| 20I | 1.58 | 0.2 | 7.90 | 0.1 | 0.5 |

Computational analysis using Solidworks® Premium 2015 Simulation software was used to produce theoretical stiffness analysis of the component. Results showed that lobe arrangement 20F above provided a component having a stiffness of 233 N/mm in the AP direction. This is comparable to the desired stiffness of 259+/−109 N/mm which corresponds most closely to that of cortical bone.

FIGS. 6A-6D show alternative lobes 20J-20K in which a profile (e.g. cross-sectional shape) of the ridges 201, as described above, is modified. In this way, the stiffness of the lobe 20 in the AP direction relative to the transverse direction may be adjusted and/or controlled.

Particularly, the lobe 20J has ridges 201, in which one such ridge 201 has flat, substantially parallel sides and a flat top. The sides of the ridge 201 have a minimum draft angle of 1°, to facilitate manufacture i.e. the ridge 201 tapers from a base towards the top of the ridge 201. The ridge 201 has dimensions of a width w of 0.838 mm and a height h of 1.58 mm. Thus, the ridge 201 has an aspect ratio R=h/w=1.58/0.838~1.89. External edges (corners) of the ridge 201 are not chamfered (i.e. square). Hence, the top of the ridge 201 is thus flat in cross-section. Internal edges (corners) of the ridge 201 are chamfered (e.g. rounded, radius 0.5 mm typical), to reduce stress-concentrations and/or facilitate manufacture.

Particularly, the lobe 20K has ridges 201, in which one such ridge 201 has flat sides arranged to taper symmetrically to a point i.e. the ridge 201 is triangular is cross-section, to facilitate manufacture. The ridge 201 has dimensions of a base width w of 0.838 mm and a height h of 1.58 mm. Thus, the ridge 201 has an aspect ratio R=h/w=1.58/0.838~1.89. Internal edges (corners) of the ridge 201 are chamfered (e.g. radiused, radius 0.5 mm typical), to reduce stress-concentrations and/or facilitate manufacture.

In this way, by modifying the profile of the ridges 201 and/or the grooves 202, the stiffness of the lobe 20 in the AP direction relative to the transverse direction may be adjusted and/or controlled.

Figure 7A:
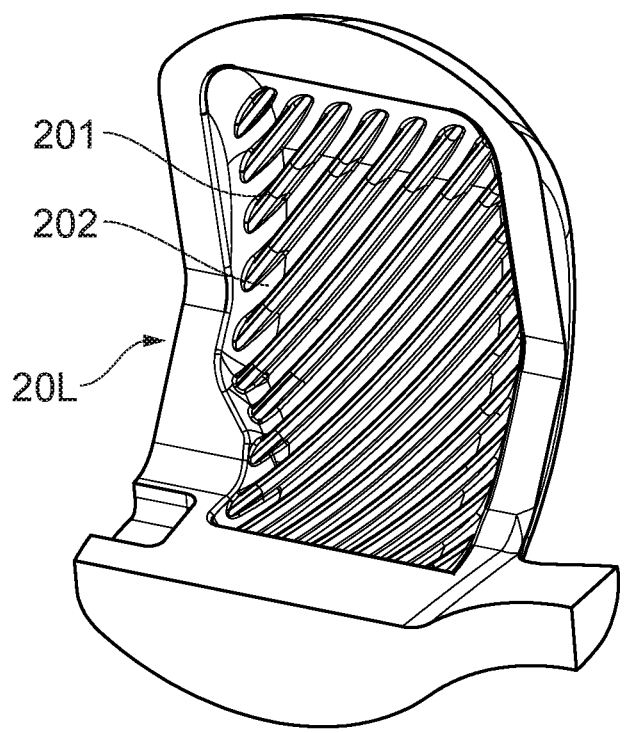
FIGS. 7A-7B schematically depict perspective views of a part of a femoral component according to other exemplary embodiments of the invention.
Figure 7B:
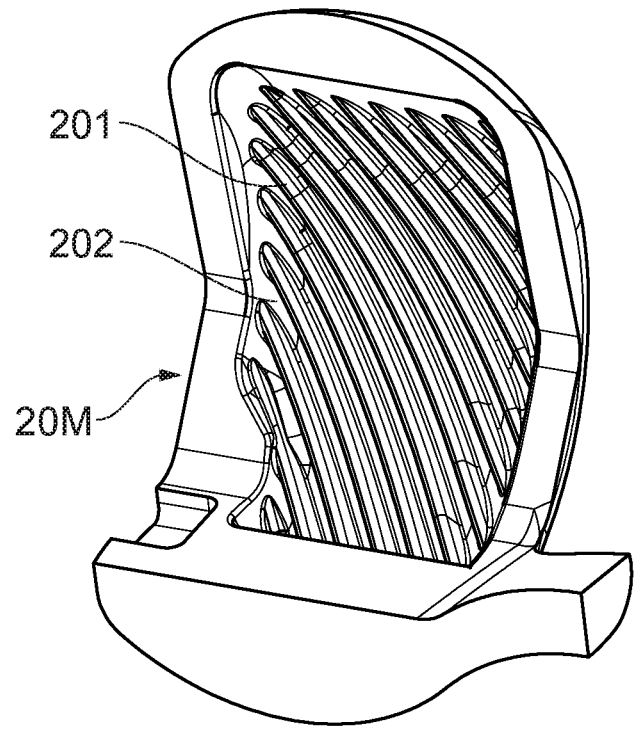

FIGS. 7A-7B show alternative lobes 20L-20M, in which an orientation of the ridges 201 and the grooves 202, as described above, is altered. In this way, the stiffness of the lobe 20 in the AP direction relative to the transverse direction may be adjusted and/or controlled.

Particularly, the lobe 20L has fifteen parallel, mutually-equispaced, straight ridges 201, that are oriented obliquely along the portion 220, in a lateral inferior to a medial superior direction. The corresponding grooves 202 are similarly oriented. Since the lobe 20L is curved and due to the oblique orientation of the ridges 201, the ridges 201 are thus helical ridges 201. In contrast, the lobe 20M has 15 parallel, mutually-equispaced, straight ridges 201, that are oriented obliquely along the portion 220, in a lateral superior to a medial inferior direction.

In this way, by altering an orientation of the ridges 201 and the grooves 202, the stiffness of the lobe 20 in the AP direction relative to the transverse direction may be adjusted and/or controlled.

Figure 8A:
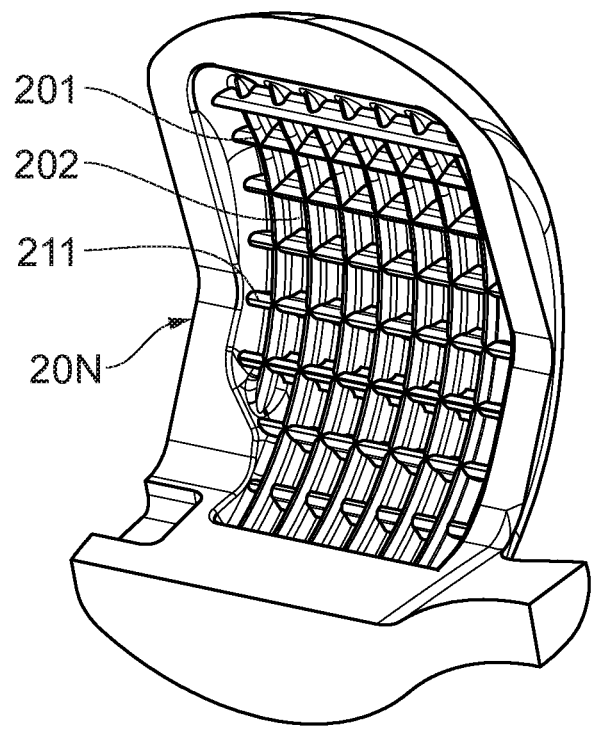
FIGS. 8A-8B schematically depict perspective views of a part of a femoral component according to other exemplary embodiments of the invention.
Figure 8B:
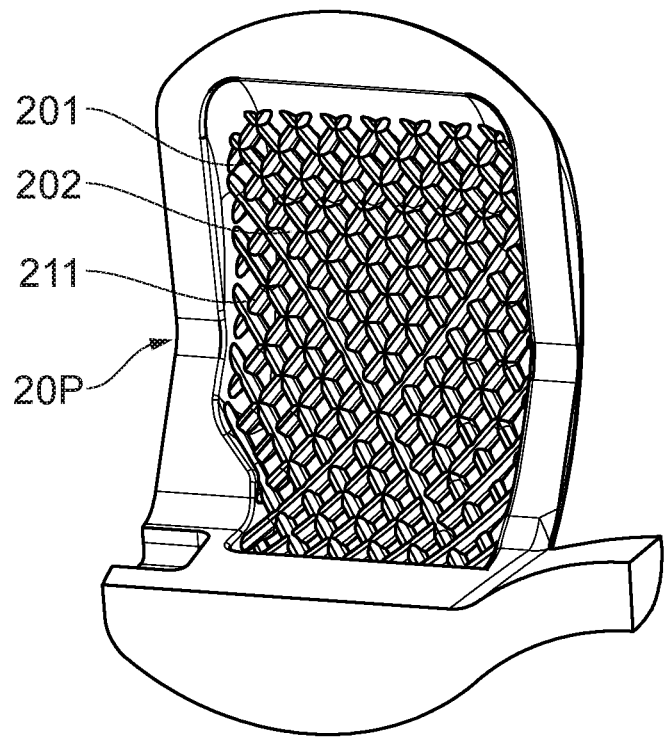

FIGS. 8A-8B show alternative lobes 20N-20P, in which other ridges 211 are provided transversely to the ridges 201 and the grooves 202, as described above. In this way, the stiffness of the lobe 20 in the AP direction relative to the transverse direction may be adjusted and/or controlled.

Particularly, the lobe 20N has seven parallel, mutually-equispaced, straight ridges 201 and a corresponding number of grooves 202, oriented in the AP direction. The lobe 20N also has eight parallel, mutually-equispaced, straight ridges 211 arranged orthogonally to the ridges 201 and the groves 202. A spacing of the ridges 211 is greater than a spacing of the ridges 201.

Particularly, the lobe 20P has fifteen parallel, mutually-equispaced, straight ridges 201 and a corresponding number of grooves 202, oriented obliquely to the AP direction. The lobe 20N also has fourteen parallel, mutually-equispaced, straight ridges 211, arranged transversely to the ridges 201 and the groves 202.

Figure 9A:
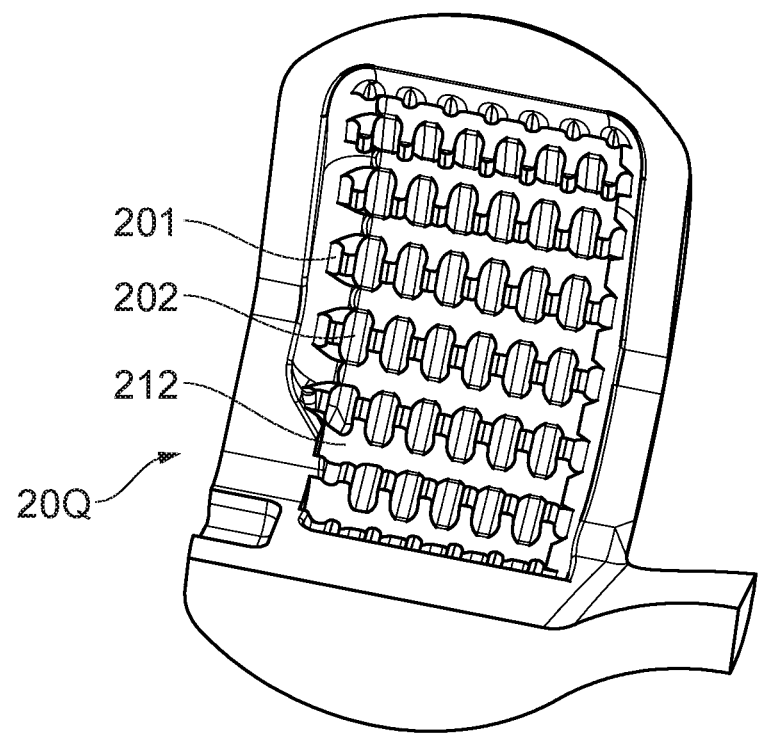
FIGS. 9A-9B schematically depict perspective views of a part of a femoral component according to other exemplary embodiments of the invention.
Figure 9B:
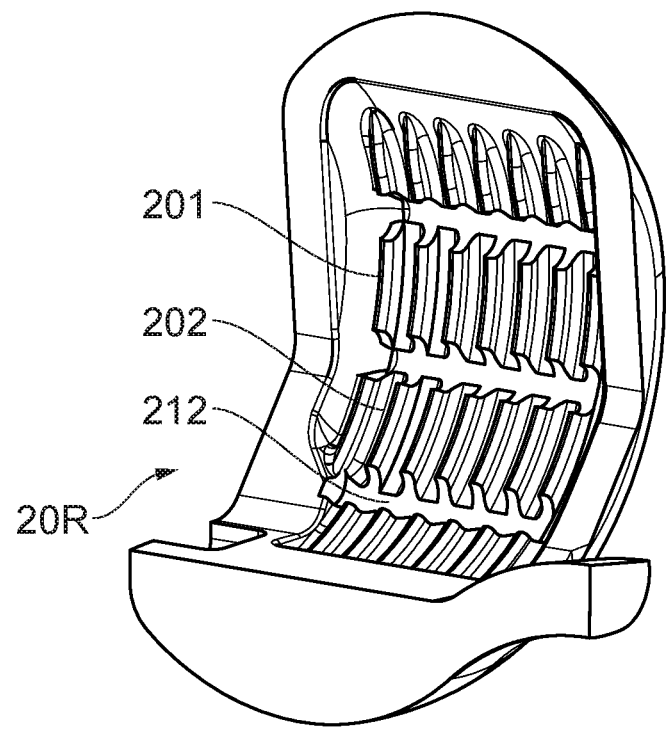

FIGS. 9A-9B show alternative lobes 20Q-20R, in which other grooves 212 are provided transversely to the ridges 201 and the grooves 202, as described above. In this way, the stiffness of the lobe 20 in the AP direction relative to the transverse direction may be adjusted and/or controlled.

Particularly, the lobe 20Q has seven parallel, mutually-equispaced, straight ridges 201 and a corresponding number of grooves 202, oriented in the AP direction. The lobe 20Q has seven parallel, mutually-equispaced, straight grooves 212, arranged orthogonally to the ridges 201 and the groves 202.

Particularly, the lobe 20R has seven parallel, mutually-equispaced, straight ridges 201 and a corresponding number of grooves 202, oriented in the AP direction. The lobe 20R has three parallel, mutually-equispaced, straight grooves 212, arranged orthogonally to the ridges 201 and the groves 202.

Figure 10A:
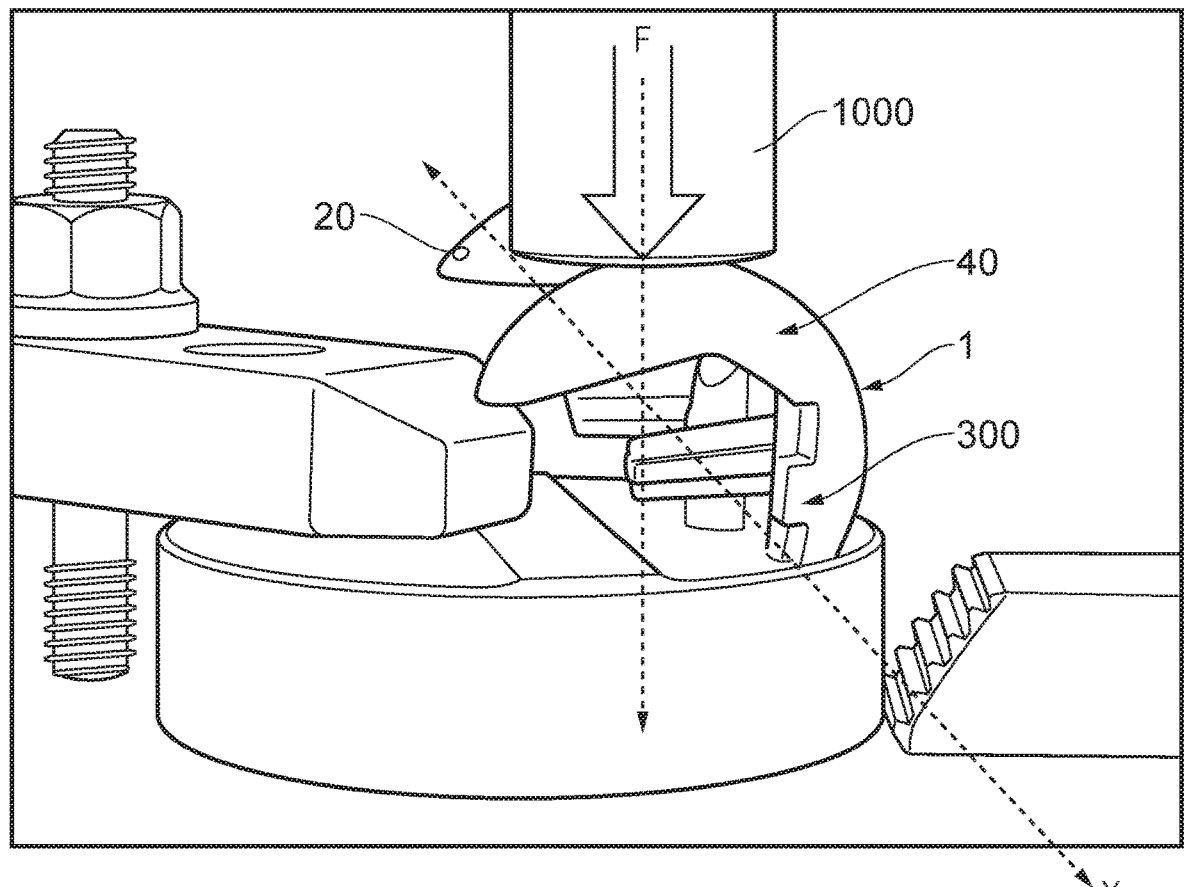
FIGS. 10A-10C depict methods of measuring a stiffness of a femoral component according to an exemplary embodiment of the invention.
Figure 10B:
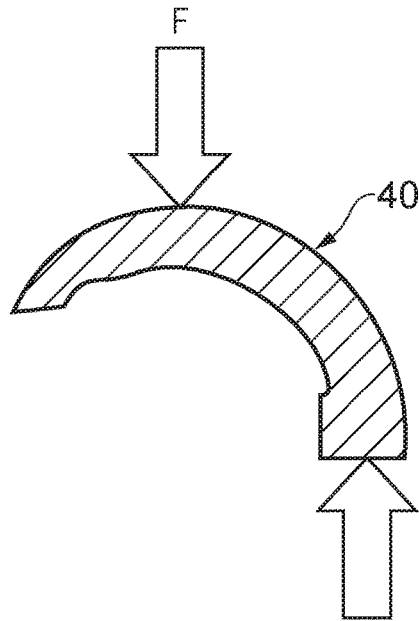
Figure 10C:
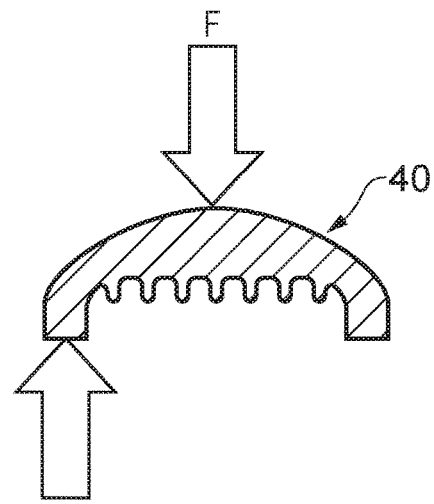

FIGS. 10A-10C depict methods of measuring a stiffness of the femoral component 1. The femoral component 1 is mounted in a universal testing machine, such that a load may be applied to the femoral component 1 in a desired direction. In this way, the stiffness of the femoral component 1 may be determined in the AP direction and in a direction transverse to the AP direction.

Particularly, as shown in FIGS. 10A-10B, the femoral component 1 is mounted such that a lobe 10, 20, 30, 40 may be cantilevered about the longitudinal part 300 i.e. about the articulation axis X. A compressive force F is applied to the outer surface (e.g. the upper most surface in this orientation) of a lobe, such as the lobe 40, and a deformation of the lobe 40 may be measured during loading. In this way, the stiffness of the femoral component in the AP direction may be determined.

As shown in FIG. 10C, the femoral component 1 is mounted such that the lobe 40 may be cantilevered about the rim e.g. about an axis transverse to the articulation axis X. The compressive force F is applied to the outer surface (e.g. the upper most surface in this orientation) of the lobe 40 and a deformation of the lobe 40 may be measured during loading.

In this way, the stiffness of the femoral component in a direction transverse to the AP direction may be determined.

Results show that, for example, for the femoral component 1 injection moulded in PEEK Optima (RTM of Invibio), having a size XS (56 mm), the AP stiffness was 191±8.46 N/mm for the medial condyle and 187±17.6 N/mm for the lateral condyle.

As would be understood by the person skilled in the art, the stiffness of the femoral component may be determined similarly according to, for example, 3 point and/or 4 point bending tests. In this way, the stiffness of the femoral component in the AP direction and/or a stiffness of the femoral component in a direction transverse to the AP direction may be determined.

Although a preferred embodiment has been shown and described, it will be appreciated by those skilled in the art that various changes and modifications might be made without departing from the scope of the invention, as defined in the appended claims and as described above.

In summary, the invention provides a knee replacement femoral component has anisotropic stiffness characteristics provided by portions provided with mutually-parallel ridges and grooves on inner surfaces of the component for attachment to a prepared femur. In a preferred arrangement, the ridges and grooves are arranged to provide an increased stiffness of the femoral component when cantilevered about the articulation axis compared with a stiffness of the femoral component when cantilevered about a transverse axis. By providing a component which has an elastic modulus similar in value to that of bone, and where the stiffness of the component when flexed about the AP axis is similar in value to the stiffness of the bone removed from the distal femur and replaced by the component, the component reduces stress shielding effects in use such that bone loss near the attached component is reduced, extending the effective life of the repair and improving attachment in use, thereby reducing a likelihood of further surgical intervention.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at least some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

What is claimed is:

1. A femoral component of a knee replacement assembly, the knee replacement assembly arranged to articulate about an articulation axis, the femoral component comprising:
   an outer surface, wherein the outer surface is arranged to define a replacement condyle; and
   an inner surface, opposed to the outer surface, wherein the inner surface is adapted for attachment to a prepared distal femur;
   wherein the inner surface comprises portions provided with mutually-parallel ridges and grooves; and
   wherein the ridges and grooves are arranged to provide an increased or reduced stiffness of the femoral component when cantilevered about the articulation axis compared with a stiffness of the femoral component when cantilevered about a transverse axis;
   wherein an aspect ratio R of a ridge of the ridges is from 1 to 30, wherein the aspect ratio R is defined as R=h/w wherein the ridge has dimensions in cross-section of a width w and a height h.

2. A femoral component according to claim 1, wherein the ridges and grooves are arranged to provide an increased stiffness of the femoral component when cantilevered about the articulation axis compared with a stiffness of the femoral component when cantilevered about a transverse axis.

3. A femoral component according to claim 1, wherein the femoral component comprises lobes comprising the portions provided with the ridges and the grooves.

4. A femoral component according to claim 1, wherein the outer surface defines a lateral condyle and a medial condyle.

5. A femoral component according to claim 4, wherein a stiffness of the lateral condyle when cantilevered about the articulation axis is greater than a stiffness of the medial condyle when cantilevered about the articulation axis.

6. A femoral component according to claim 1, wherein the ridges and the grooves are oriented in an anterior-posterior (AP) direction, transverse to the articulation axis.

7. A femoral component according to claim 1, wherein the ridges are mutually equidistantly spaced.

8. A femoral component according to claim 1, wherein the ridges are discontinuous.

9. A femoral component according to claim 1, wherein five to fifteen ridges are provided.

10. A femoral component according to claim 1, wherein the femoral component is formed from a polymeric composition, the polymeric composition having an elastic modulus from 3000 MPa to 5000 MPa.

11. A femoral component according to claim 10, wherein the polymeric composition comprises one or more polymers selected from a group comprising: polyarylketone, polyacetal, polyester, polyamide, polyurethane, polycarbonate, polyimide and polysulfone.

12. A femoral component according to claim 10, wherein the polymeric composition is a reinforced polymeric composition, comprising one or more fillers selected from a group consisting of: fibres, particles and platelets.

13. A femoral component according to claim 1, wherein stiffness of the femoral component when cantilevered about the articulation axis is from 100 N/mm to 400 N/mm.

14. A femoral component according to claim 1:
   wherein the ridges and grooves are arranged to provide an increased stiffness of the femoral component when cantilevered about the articulation axis compared with a stiffness of the femoral component when cantilevered about a transverse axis;
   wherein the femoral component comprises lobes comprising the portions provided with the ridges and the grooves;
   wherein the outer surface defines a lateral condyle and a medial condyle;
   wherein the ridges and the grooves are oriented in an anterior-posterior, (AP), direction, transverse to the articulation axis;
   wherein an aspect ratio R of a ridge of the ridges is from 1 to 30, wherein the aspect ratio R is defined as R=h/w wherein the ridge has dimensions in cross-section of a width w and a height h;
   wherein the femoral component is formed from a polymeric composition, the polymeric composition having an elastic modulus from 3000 MPa to 5000 MPa; and
   wherein stiffness of the femoral component when cantilevered about the articulation axis is from 100 N/mm to 400 N/mm.

* * * * *

UNITED STATES PATENT AND TRADEMARK OFFICE
CERTIFICATE OF CORRECTION

PATENT NO. : 10,918,491 B2  
APPLICATION NO. : 16/081360  
DATED : February 16, 2021  
INVENTOR(S) : Stephen Bonham et al.

Page 1 of 1

It is certified that error appears in the above-identified patent and that said Letters Patent is hereby corrected as shown below:

On the Title Page

Please correct Item (30) Foreign Application Priority Data as follows:  
(30)  
Mar. 2, 2016     (GB) ...............................1603608.9

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*